Figure 1:
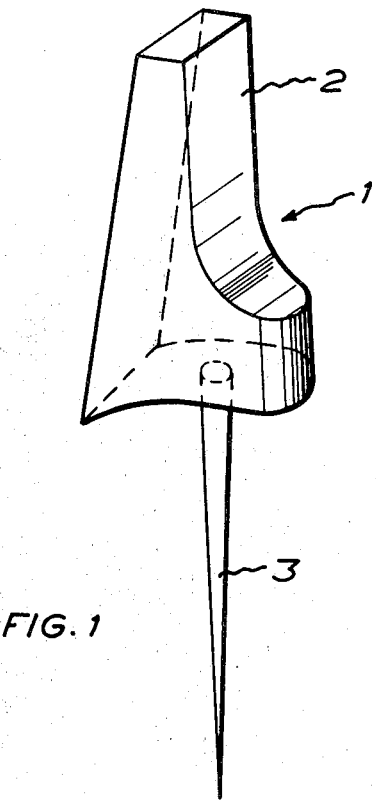

United States Patent [19]

Ericson

[11] 4,355,978
[45] Oct. 26, 1982

[54] PATRIX FOR THE PRODUCTION OF A GOLD CORE FOR A PREPARED ROOT-FILLED TOOTH

[76] Inventor: Dan W. Ericson, Ehrensvärdsgatan 6, S-212 13 Malmö, Sweden

[21] Appl. No.: 197,705

[22] Filed: Oct. 16, 1980

[30] Foreign Application Priority Data

Oct. 16, 1979 [SE] Sweden ............................ 7908538

[51] Int. Cl.$^3$ ................................................ A61C 5/08
[52] U.S. Cl. .................................... 433/220; 433/223
[58] Field of Search ............... 433/220, 221, 219, 223, 433/224, 218, 214, 40, 226, 34, 37, 48; 264/19, 16

[56] References Cited

U.S. PATENT DOCUMENTS

| | | | |
|---|---|---|---|
| 641,930 | 1/1900 | Brewster | 433/220 |
| 731,594 | 6/1903 | Mosley | 433/220 |
| 751,592 | 2/1904 | Whiteside | 433/220 |
| 907,949 | 12/1908 | Ballou | 433/220 |
| 983,579 | 2/1911 | Taggart | 433/226 |
| 1,037,489 | 9/1912 | Kelsey | 433/220 |
| 1,140,539 | 5/1915 | Skinner | 433/220 |
| 1,397,067 | 11/1921 | Williams | 433/221 |
| 2,536,669 | 1/1951 | Thau-Jensen | 433/221 |
| 3,949,476 | 4/1976 | Kahn | 433/220 |

FOREIGN PATENT DOCUMENTS 1131191 2/1957 France ............................ 433/220

*Primary Examiner*—Gene Mancene
*Assistant Examiner*—John J. Wilson
*Attorney, Agent, or Firm*—Fleit & Jacobson

[57] ABSTRACT

In a method for the production of a gold core for a prepared root-filled tooth, the prepared root canal of the tooth is filled with a gasifiable setting impression material. A prefabricated core patrix, preferably of plastic, which consists of a core portion and a dowel portion, is inserted in the impression material which is allowed to set around the dowel portion for the formation of a core pattern. The core pattern is removed from the tooth and is embedded in a mold material which is heated for the gasification of the pattern, whereupon a gold core is cast in the mold formed after the gasification of the pattern.

A core patrix for the production of a gold core for a prepared root-filled tooth is made as a single piece and consists of a core portion and a dowel portion which has a substantially smaller transverse dimension than the prepared root canal of the tooth. The core patrix is preformed and consists of a gasifiable material. The core portion serves as a pattern for a gold core intended for the fixation of a tooth crown and the dowel portion is insertable in the root canal of the tooth in order there to form a fixation for a gasifiable setting impression material applied to the root canal, the core patrix and the set impression material applied to the dowel portion being usable as a casting pattern for the gold core.

1 Claim, 2 Drawing Figures

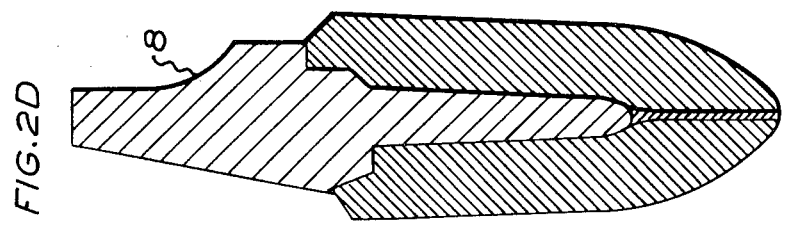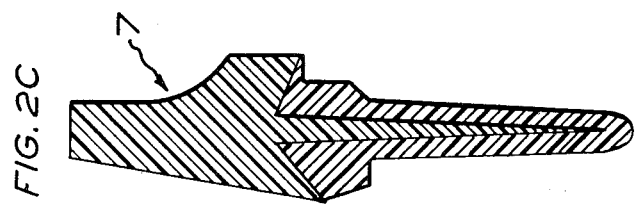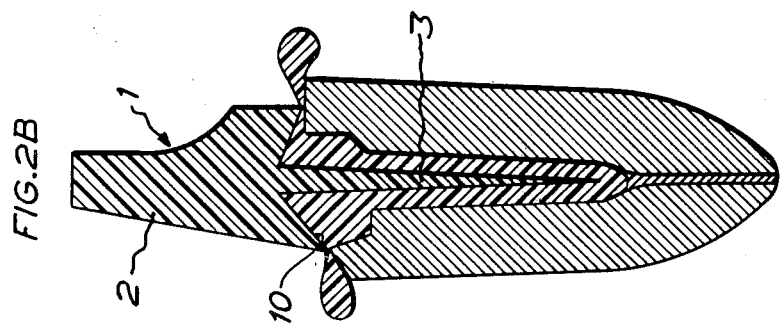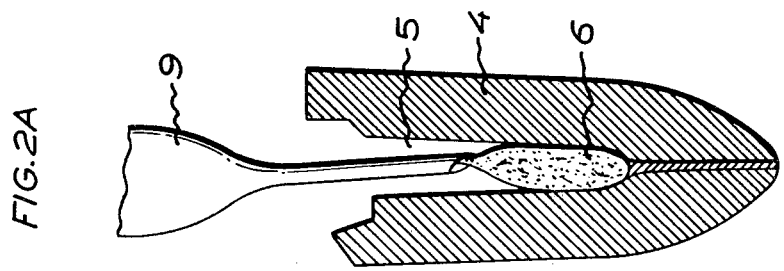

PATRIX FOR THE PRODUCTION OF A GOLD CORE FOR A PREPARED ROOT-FILLED TOOTH

The present invention relates to a method for the production of a gold core for a prepared root-filled tooth and to a core patrix for carrying out the method, which core patrix has a core portion and a dowel portion, said core portion substantially corresponding to the shape of the upper part of the finished gold core.

In restorative dentistry, gold cores have long been in use to replace lost tooth substance and to serve as a fixation for an artificial tooth crown on a root-filled tooth. Attempts have been made with such a gold core to immitate the preparation of a vital tooth where the extension of the pulp and the strength of the dentine have been normative of how thin it has been possible to make the preparation. Since the strength of gold is considerably greater than that of dentine, it is however possible to make the gold core much thinner without jeopardizing the strength of the core. The possible thinness of a gold core depends on the following factors: (1) The strength of the gold. (2) The retention of the artificial tooth crown. (3) The shape of the root canal; the core should not be made narrower than the root canal lumen for reasons of retention and strength, on the one hand, and for reasons of practical manufacture, on the other.

In regard of retention, the vertical dimension of the core and the number of approximately parallel surfaces on the core are of paramount importance, whereas the total surface of the core is of lesser importance.

Since the crown replacement is formed after the shape of the core, it most often is no limiting factor for the configuration of the gold core, provided there is enough space for the crown material. This means that a core, as to the supragingival part facing the crown replacement, can be standardized to advantage if the part facing the tooth and the root canal at the same time can be given an individual shape.

The production of cores for root-filled teeth is today a time-consuming task both for the dentist and for the dental technician and there are difficulties in attaining optimum fit for the core in the prepared root canal.

In a conventional method for the preparation of a gold core, a copper ring is placed on the prepared tooth at the upper mouth of the pre-bored root canal. A pin or dowel is inserted through the copper ring so as to extend into the root canal. An impression material is thereafter pressed down into the copper ring and the root canal. After hardening of the impression material, the impression of the root canal is sent to a dental technician who makes a plaster model or pattern of the root canal. From this plaster model, he makes a wax core by supplying wax to the plaster model of the root canal. The wax is supplied in such an amount that the dental technician can make a pattern of the core portion which is above the root canal. The wax pattern is thereafter embedded in a casting compound, baked and replaced by gold. This method is time-consuming and hence expensive. Since the casting pattern is not made in the patient's mouth, there is also a risk that the finished gold core does not fit accurately in the root-filled tooth.

In a further method, the preparation of the plaster pattern and the wax core has been dispensed with. Instead, use is made of a self-polymerizing plastic, for instance Duralay manufactured by Reliance Dental MFG. CO., USA, or casting wax. The plastic is supplied in the same way as above through the copper ring to the root canal, whereupon an extensive adjustment and shaping operation is carried out in the patient's mouth. The thing is that the dentist himself shapes the upper part of the core pattern. The set plastic pattern is then sent to the dental technician who makes a gold core by casting from the plastic pattern. It is true that this method is an improvement as compared with the first-mentioned method, but the extensive adjustment work in the patient's mouth is a material drawback.

The object of the present invention is to provide a method for the production of a gold core for crown and bridge support with the aid of a plastic core patrix.

According to the invention, this object is achieved by a method characterized by filling the prepared root canal of the tooth with a gasifiable setting impression material; inserting a preformed core patrix, preferably of plastic, which consists of a core portion and a dowel portion, in said impression material which is allowed to set around said dowel portion for the formation of a core pattern consisting of said core patrix and said impression material secured to said dowel portion; removing said core pattern from the tooth and embedding it in a mold material; heating the mold material for gasification of said pattern; and casting a gold core in the mold formed upon gasification of said pattern.

Another object of the invention is to provide a core patrix for the production of a gold core.

According to the invention, this object is achieved by the provision of a core patrix which is characterized in that said core portion and said dowel portion are made as one piece from a gasifiable plastic material and that the dowel portion has a substantially smaller thickness than the root canal and, after the insertion of the dowel portion in a root canal filled with an impression material and after setting of said impression material on said dowel portion, together with said impression material will form a core pattern from which the gold core is cast.

According to the invention, a prefabricated core patrix is used to facilitate the production of a pattern for the gold core. The core patrix is made of plastic which is gasified at 600°–800° C. without leaving any residues. The core patrix approximately fits to the prepared tooth and by filling the space between the tooth and the core patrix with a self-polymerizing plastic or casting wax, there is obtained a complete pattern for the production of a gold core with accurate fit.

The core patrix may conceivably be made in five different sizes which fit most incisive, canine and molar teeth.

The advantages of the present invention reside in that the time of manufacture is reduced both for the dentist and for the dental technician, less material is required for the dentist and the dental technician, and optimum fit of the core is obtained. This also entails reduced manufacturing costs.

The invention will be described in greater detail hereinbelow with reference to the accompanying drawings showing one embodiment of the invention and in which:

FIG. 1 shows a core patrix according to the invention with a core portion and a dowel portion, and FIGS. 2A–D illustrate different steps in the production of a gold core.

Referring to the drawings, FIG. 1 shows a core patrix 1 for the production of a gold core for an incisive tooth. The core patrix consists of an upper core portion 2 and a lower dowel portion 3. The core patrix is made as a single piece from a gasifiable plastic, for instance polymethyl methacrylate, and the core portion 2 serves as a pattern for that part of the finished gold core which is to form a fixation for a tooth crown. Thus, the core portion is so constructed as to provide maximum retention for the crown and enough space for gold and facade material. The core portion in principle is in finished shape but may optionally be adjusted vertically or laterally. The dowel portion 3 will serve as a fixation for a self-polymerizing impression plastic with which the prepared root-filled tooth is filled. The length of the dowel is adjusted to the depth of the root canal. It should be noted that core patrixes for canine and molar teeth have a corresponding configuration, except that the core portions are adapted to suit crown replacements for canine and molar teeth, respectively.

FIGS. 2A–D illustrate the method of the invention for producing a core pattern for a gold core with the aid of a core patrix according to FIG. 1. FIG. 2A shows a root-filled tooth 4 whose root canal 5 has been reamed for receiving a gold core. After the preparation of the tooth 4, a core patrix with approximative fit to the tooth 4 is selected. If need be, the length of the dowel portion is cut to proper size. The walls of the root canal 5 are vaselined sufficiently to prevent impression plastic from sticking to the walls. Self-polymerizing impression plastic 6 is thereafter supplied to the root canal by means of a plastic tube 9, for instance a so-called Jiffy tube. It is essential that the root canal 5 be filled as far as the upper part of the tooth. The selected core patrix 1 is inserted with its dowel portion 3 into the root canal 5 (FIG. 2B) filled with impression plastic. As shown in FIG. 2B, the bottom portion 10 of core portion 2 is recessed to confine the impression material to the dowel portion 3. Excess plastic will then well up over the tooth rim. The plastic is allowed to set to some extent. While the plastic is still soft, the formed core pattern 7 (FIG. 2C) is moved up and down in the canal a few times in order to prevent plastic material from sticking to the root canal. Excess plastic is removed by means of a scalpel or a Nyström type carver. When the plastic has set completely, the height and width of the core portion can be adjusted, if desired. The core pattern 7 is thereafter sent to the dental technician, to be embedded and cast. Since gasifiable plastics are used for both the core patrix and the impression plastic, a mold for casting the gold core can be obtained by heating the core pattern embedded in a casting compound. After casting of a gold core 8, it is cemented to the tooth 4 (FIG. 2D), whereupon the preparation is optionally trimmed.

As is obvious, the method for producing a gold core for canine or molar teeth is carried out in the same manner as described above but with the use of a preformed core patrix whose upper portion is suited to serve as a pattern for a gold crown for a canine or a molar tooth.

What I claim and desire to secure by Letters Patent is:

1. A core patrix for the production of a gold core for a prepared root-filled tooth having a root canal, said core patrix comprising: a single piece made from a gasifiable material, said single piece having a core portion and a dowel portion, said core portion corresponding to and defining the shape of the upper part of the finished gold core, said dowel portion having a substantially smaller thickness than the root canal, said patrix, after the insertion of said dowel portion in a root canal filled with a gasifiable impression material and after setting of said impression material on said dowel portion, together with said impression material will form a core pattern from which the gold core is cast, said core portion including a recessed portion facing said dowel portion and the root canal, said recessed portion confining said impression material to said dowel portion.

* * * * *